United States Patent [19]

Khalil et al.

[11] Patent Number: 4,761,279

[45] Date of Patent: Aug. 2, 1988

[54] SHAVING CREAM FORMULATIONS

[75] Inventors: Ezzat N. Khalil, River Forest, Ill.; Michael K. Edwards; Howard K. Hobbs, both of Kingsport, Tenn.

[73] Assignee: Eastman Kodak Company, Rochester, N.Y.

[21] Appl. No.: 32,276

[22] Filed: Mar. 31, 1987

[51] Int. Cl.$^4$ ................................................. A61K 7/15
[52] U.S. Cl. .................................................... 424/73
[58] Field of Search ................................... 424/70–73

[56] References Cited

U.S. PATENT DOCUMENTS 3,453,116 7/1969 Freund ..................................... 99/98
3,673,106 6/1972 Jonas et al. ........................... 252/356

*Primary Examiner*—Nancy A. B. Swisher
*Attorney, Agent, or Firm*—John F. Stevens; William P. Heath, Jr.

[57] ABSTRACT

Disclosed are new shaving cream formulations and their preparation. The formulations incorporate salts of fatty acid esters of lactylic acid, saturated monoglycerides, propylene glycol monoesters and humectant as the essential ingredients.

15 Claims, No Drawings

4,761,279

SHAVING CREAM FORMULATIONS

FIELD OF THE INVENTION

This invention relates to new shaving cream formulations and their preparation. More particularly, the invention relates to soapless and non-detergent shaving cream formulations incorporating salts of fatty acid esters of lactylic acid, saturated monoglycerides, propylene glycol monoesters and humectant as the essential ingredients.

BACKGROUND OF THE INVENTION

The removal of unwanted hair from the human epidermis is commonly accomplished by shaving with a razor which, in the male, is a daily exercise for the removal of facial hair and in the female is a regular, but less frequent exercise applied to areas such as the legs and underarms. A wide variety of soaps, creams and oils are available to facilitate the shaving process and lessen the discomfort and trauma to the skin experienced by the razor's actions. Shaving creams are, by far, the preparation of choice for facilitating the act of shaving and lessen the arbrasion, irritation, and localized trauma which, to a greater or lesser extent, is associated with hair removal by shaving. Shaving creams are lather-producing, either through the action of a brush or as propelled from an aerosol container. Both are commonly formulated using soap and/or detergents as the lather forming agent, the latter or brushless shaving cream are oil-in water emulsions of the cream type.

Shaving cream is commonly a lather-forming, soap-based formulation further modified for application with a shaving brush or as a soap-based and/or detergent foam from an aerosol dispenser. Such formulations should provide an easy and rapid production of copious lather; the lather should be resistant to collapse while on the face; there should be a softening of the hair in a viscosity sufficient to hold the hair erect; the lather should provide sufficient lubrication for the razor blade and there should be minimum irritation of the skin. Soaps, particularly those derived from coconut oil, can readily provide a fast lather build-up and experience has shown that those soaps derived from palm oil provide a strong lather. Accordingly, common shaving cream formulations usually contain mixtures of such soaps and/or detergents to meet the requirements of the quality of shaving lather to be produced. Unfortunately, the inclusion of such soaps and/or detergents rendered the shaving cream formulation fairly basic with a pH from about 8 to 10. Since the normal pH of human skin is in the range of pH 4.5, the so-called skin "acid mantle", the application of a shaving preparation of high alkalinity is often irritating to the skin. Although the soap-based and/or detergent shaving cream formulations readily provide a lather of the requisite consistency their natural alkalinity is a significant problem that contributes to the traumatization of the skin during the shaving process.

From the foregoing, it is evident that the requirements of a preferred cream for good lathering properties on the one hand but formulated from non-irritating chemicals presents a problem of considerable dimension to those skilled in the art.

The present invention provides shaving cream formulations that can be readily foamed into a rich shaving lather, are not irritating to the skin, are non-toxic and have the other desired characteristics of shaving stated above.

This invention further provides non-soap and non-detergent containing, non-irritating shaving cream formulations that can be ideally dispensed and applied as an aerosol foam.

This invention also provides a non-soap and non-detergent containing, non-irritating, readily dispensable, shaving cream formulation prepared from safe, non-toxic, economical ingredients.

DESCRIPTION OF THE INVENTION

According to the present invention, shaving cream formulations are provided which comprise:
(a) about 0.2 to about 20 parts by weight of at least one salt of a fatty acid ester of lactylic acid,
(b) about 1.2 to about 56 parts by weight of at least one saturated monoglyceride of a straight chain fatty acid having from 8 to 22 carbon atoms and an iodine value of 0 to about 20,
(c) about 0.8 to about 48 parts by weight of at least one saturated monoester of propylene glycol and a straight chain fatty acid having from 8 to 22 carbon atoms and an iodine value of 0 to about 20,
(d) about 1 to about 90 parts by weight of a polyhydroxylated humectant,
(e) 0 to about 25 parts by weight of an unsaturated monoglyceride of at least one straight chain fatty acid having from 8 to 22 carbon atoms and an iodine value of about 30 to about 110, and
(f) 0 to about 95 parts by weight water.

The consistency of the shaving cream formulations can range from a pasty substance which may require the addition of water to a viscous, pourable liquid.

Preferably, the shaving cream formulations contain at least some unsaturated monoglyceride described in (e) above to give the formulations increased lubricating properties. It is also preferred that the formulations, when used, contain an amount of water to give the formulations a pleasing consistency. However, depending on the form of the formulation when packaged, water can be omitted and added at the time of use, or the quantity of water can be adjusted to give the product the desired form.

The following formulation is a preferred embodiment of the invention for the shaving cream ready for application, especially from aerosol, to the body prior to shaving:
(a) about 0.4 to about 1.5 parts by weight of at least one salt of a fatty acid ester of lactylic acid,
(b) about 1.40 to about 4.50 parts by weight of at least one saturated monoglyceride of a straight chain fatty acid having from 8 to 22 carbon atoms and an iodine value of 0 to about 20,
(c) about 2.0 to about 6.2 parts by weight of at least one saturated monoester of propylene glycol and a straight chain fatty acid having from 8 to 22 carbon atoms and an iodine value of 0 to about 20,
(d) about 2 to about 10 parts by weight of a polyhydroxylated humectant,
(e) about 1 to about 4 parts by weight of an unsaturated monoglyceride of at least one straight chain fatty acid having from 8 to 22 carbon atoms and an iodine value of about 60 to about 110, and
(f) 74 to about 93 parts by weight water.

Salts of fatty acid esters of lactylic acid employed in the invention are well known in the art and available commercially. They may be prepared by reacting lactylic acid with acids by known conventional condensation processes, such as those disclosed in U.S. Pat. No. 2,733,252, incorporated herein by reference. Illustrative of such salts are alkali, alkaline earth, ammonium, and in particular, the sodium, potassium, and calcium salts of fatty acid esters wherein the fatty acid contains 14 to 22 carbon atoms. Such fatty acids include palmitic, stearic, oleic and the like. Particularly preferred are sodium stearoyl-2-lactylate and calcium stearoyl-2-lactylate.

The saturated monoglycerides useful in the present invention have an iodine value of 0 to about 20. Preferred saturated monoglycerides include those having iodine values of 0 to about 5, those made by interesterification of glycerine with fully saturated fats or oils such as tallow, palm oil, cottonseed oil, soybean oil, peanut oil, sesame oil and the like. These monoglycerides usually contain monoesters at a concentration of at least 90% by weight. Alternatively, such monoglycerides can be prepared by reacting glycerine with straight chain fatty acids such as those found in vegetable oils and animal fats having from about 8 to about 22 carbon atoms, and saturated to an extent to result in an iodine value of about 0 to about 5. Such monoglycerides are commerically available, for example, Myverol ® 18-00, 18-04, 18-06 and 18-07 distilled monoglycerides, products of Eastman Chemicals Products. Inc.

Procedures for preparing high purity monoglycerides useful in the present invention are disclosed in U.S. Pat. Nos. 2,634,234, 2,634,278 and 2,634,279, incorporated herein by reference.

The propyleneglycol monoester should be 1,2-propyleneglycol monoester, and have an iodine value of 0–20, preferably 0 to about 5. The monoester is advantageously purified after usual preparation by molecular distillation. Stearic acid is the preferred fatty acid moiety of the ester, but other fatty acid moieties deriving from fully hydrogenated oils and fats, which after hydrogenation possess a high content of stearic acid are also useful. Unsaturated fatty acid moieties are not suitable. Examples of fats and oils from which the propyleneglycol monoester can be derived are soybean oil, cottonseed oil, lard, and tallow. Hydrogenation of the fatty acid moieties can be performed before or after formation of the propylene glycol monoester. Their principal fatty constituent after hydrogenation is stearic acid.

The unsaturated monoglycerides of the invention include the distilled monoester products made by interesterification of glycerine with fats and oils such as sunflower oil, tallow, palm oil, cottonseed oil, soybean oil, peanut oil and the like. Such distilled monoester products usually contain monoesters at a concentration of at least about 90% by weight. Alternatively, such monoglycerides can be prepared by reacting glycerine with straight chain fatty acids such as those found in vegetable oils and animal fats having from 8 to 22 carbon atoms, and saturated to an extent to result in an iodine value of about 30 to 120, preferably about 60 to 110. Such monoglycerides are commercially available, for example, Myverol ® 18-50, 18-85 and 18-92 distilled monoglycerides, products of Eastman Chemical Products, Inc.

It is essential that the shaving cream formulation of this invention contain at least one polyhydroxylated humectant, preferably at a concentration of about 2 to 10 parts by weight. Typically, humectants such as propylene glycol, diethylene glycol, glycerine and the like may be used. Glycerine is particularly preferred.

The amount of water present in the shaving formulations of the invention depends upon whether a concentrate or ready-to-use shaving cream composition is prepared. The concentrates usually contain about 30 to less than 74 parts by weight, depending on desired product consistency, while the ready-to-use shaving cream usually contain 74 to about 93 parts by weight, preferably about 85 to about 90 parts by weight. Preferably, the water is distilled or deionized.

Any of the shaving cream formulations of this invention may be prepared using conventional techniques and apparatus. Heating may be required during any stage of the preparation. The preferred proportions of all of the ingredients, including water, are mixed in a laboratory or industrial mixer suitable for mixing creams and the like. Following mixing, the cream is packaged for dispensing. When dispensing is to be achieved using aerosol cans, it has been found that any of the conventional propellants can be used; in particular, hydrocarbons such as methane, ethane, isobutane, butane, propane, and pentane, and lower molecular weight fluorinated hydrocarbons.

In preparing the preferred compositions according to this invention, (a) the salt of fatty acid ester of lactylic acid, (b) saturated monoglyceride, and (c) propylene glycol monoester must be melt-blended, and preferably powdered prior to use in the formulation. Such powdered blends are commercially available as Myvatex ® Texture Lite food emulsifier, product of Eastman Chemical Products, Inc. If the unsaturated monoglyceride is used, it must be dissolved or melt blended with glycerine by heating together to temperatures of about 100°–120° F. (38°–49° C.) prior to its addition to the other ingredients to avoid gelling. This is especially important when water is present as an ingredient. Water is preferably added to the mixture of (a), (b) and (c), and then the mixture of humectant and unsaturated monoglyceride is mixed therewith with stirring. In preparing some of the other formulations, (a), (b) and (c) are melt-blended with the humectant and unsaturated monoglyceride (if used). The shaving cream formulation can then be prepared by addition of hot water.

A convenient and unique feature of this invention is the adaptability of the formulation to a method of preparation in concentrated form. The concentrated formulation may be prepared by simply mixing the ingredients in conventional equipment. The concentrated formulation, typically containing about 1.7 to about 4.5 parts by weight of the alkali metal salt of a fatty acid ester of lactylic acid, about 5.2 to about 13.9 parts by weight saturated monoglyceride, about 7.2 to about 19.2 parts by weight propylene glycol monoester, about 8.0 to about 21.6 parts by weight of the polyhydroxylated humectant, about 4.0 to about 10.8 parts by weight of the unsaturated monoglyceride and about 30 to less than 74 parts by weight of water, can conveniently be used as a stock formulation which can be further diluted with an appropriate quantity of water to prepare shaving cream products of the invention ready for packaging, dispensing and use. This feature of the invention significantly contributes to the manufacturing ease of the final formulation thereby improving the cost of the overall manufacturing process.

The shaving cream prepared according to this invention produces a rich, creamy, non-irritating foam when used by application to the skin prior to shaving in a conventional manner. The pH of the cream is 4.5 to 5.5, essentially the same as that of the natural pH of the skin.

The shaving cream has excellent lather, wetting and lubricating properties while offering to the user a formulation more compatible with the natural chemistry of the skin and therefore significantly less irritating than ordinary shaving creams.

The following examples are included to further illustrate this invention:

EXAMPLE 1

Preparation of Shaving Cream Concentrate

The following ingredients are weighed into a Hobart Mixer (Model N-50): a powder containing 3.23 parts by weight of the sodium salt of stearoyl-B 2-lactylic acid, 9.95 parts by weight saturated monoglyceride, 13.72 parts by weight propylene glycol monoesters and 50 parts by weight water; a melt blend of 15.4 parts by weight of glycerine and 7.7 parts by weight of Myverol ® 18-92 monoglyceride (an unsaturated sunflower oil monoglyceride having an iodine value of 110, produced by Eastman Chemical Products, Inc.). The ingredients are mixed with heating to produce a homogeneous blend. Fragrance, preservatives, colorants or the like, known to those skilled in the art, may be added as desired.

Shaving cream concentrates having a paste consistency are prepared in a manner similar to that described for Example 1 according to the following formulations:

| Example | Parts by Weight | | | | | |
|---|---|---|---|---|---|---|
|  | A | B | C | Humectant | D | H$_2$O |
| 2 | 9.6 | 29.6 | 40.8 | 20 | 0 | 0 |
| 3 | 6.5 | 19.9 | 27.4 | 30.8 | 15.5 | 0 |
| 4 | 3.9 | 11.9 | 16.4 | 18.4 | 9.2 | 40 |
| 5 | 1.7 | 5.2 | 7.2 | 8 | 4.0 | 73.9 |

Example
1 = 50% Water Concentrate
2 = Anhydrous Concentrate
3 = Anhydrous Concentrate With Unsaturated Monoglyceride
4 = 40% Water Concentrate
5 = Pumpable Viscous Liquid
A - Sodium salt of stearyl lactylic acid
B - Saturated Monoglyceride
C - Propylene Glycol Monoester
D - Unsaturated Monoglyceride The formulation of Examples 1-5 are mixed with water ranging from 2.5 to 19 parts by weight water per part of formulation at the time of use. All are effective as shaving cream formulations, are readily foamable, into a rich lather and are not irritating to the skin. Formulations containing no unsaturated monoglycerides do not have the lubricating characteristics of the ones containing unsaturated monoglycerides.

EXAMPLE 6

Preparation of Shaving Cream Product

The following ingredients are weighed into a Hobart Mixer (Model N-50): a powder of 0.84 parts by weight of the sodium salt of stearoyl-2-lactylic acid, 2.59 parts by weight saturated monoglyceride and 3.57 propylene glycol monoester and 87 parts water; a melt blend of 2 parts by weight unsaturated monoglyceride and 4 parts by weight of glycerine. The ingredients are mixed with heating until a homogeneous blend is achieved. Optionally, fragrance and/or preservative may be added. The completed cream may be used as prepared or may be packaged in an aerosol can using conventional propellants.

Testing of the shaving qualities of this shaving cream show that the cream has good lubricating characteristics, does not burn the skin and leaves the skin smooth with a pleasant feel.

Shaving cream formulations having a light, foamy consistency, ready for use are prepared in a manner similar to that described in Example 6 according to the following formulations:

| Example | Parts by Weight | | | | | |
|---|---|---|---|---|---|---|
|  | A | B | C | Humectant | D | H$_2$O |
| 7 | 0.48 | 1.48 | 2.04 | 1 | 0 | 96 |
| 8 | 0.48 | 1.48 | 2.04 | 1 | 1 | 94 |
| 9 | 1.44 | 4.44 | 6.12 | 8 | 4 | 76 |

A - Sodium salt of stearyl lactylic acid
B - Saturated Monoglyceride
C - Propylene Glycol Monoester
D - Unsaturated Monoglyceride If it is desired to use the shaving cream formulations as an aerosol, the following concentrations are preferred:

| Ingredient | Parts by Weight, Exclusive Of Propellant |
|---|---|
| (a) metal salt of fatty acid ester of lactylic acid | .70–1.0 |
| (b) saturated monoglyceride | 2.25–3.0 |
| (c) propylene glycol monoester | 3–4 |
| (d) humectant | 3–5 |
| (e) unsaturated monoglyceride | 1.5–2.5 |
| (f) water | 89.55–84.5 |

The aerosol formulations may be produced using conventional techniques well known in the art. For example, the ingredients are pressurized in a container with a conventional propellant, using a conventional discharge nozzle. Tests indicate that this aerosol formulation has all the desired characteristics of shaving cream mentioned herein.

Anywhere "parts by weight" is used, it is intended to be based on the total weight of salts of fatty acid esters lactylic acid, saturated monoglyceride, propylene glycol monoesters, humectant, and unsaturated monoglyceride and water if used.

The iodine values specified herein are measured in accordance with AOCS Official Method Cd 1-25 (rev. April 1956), Official and Tentative Methods of the American Oil Chemists Society, 2nd ed., additions and revisions 1947 through 1963, inclusive.

The invention has been described in detail with particular reference to preferred embodiments thereof, but it will be understood that variations and modifications can be effected within the spirit and scope of the invention.

We claim:
1. A shaving cream composition comprising
 (a) about 0.2 to about 20 parts by weight of at least one salt of a fatty acid ester of lactylic acid,
 (b) about 1.2 to about 56 parts by weight of at least one saturated monoglyceride of a straight chain fatty acid having from 8 to 22 carbon atoms and an iodine value of 0 to about 20,
(c) about 0.8 to about 48 parts by weight of at least one propylene glycol monoester of a saturated straight chain fatty acid having from 8 to 22 carbon atoms and an iodine value of 0 to about 20,
(d) about 1 to about 90 parts by weight of a polyhydroxylated humectant,
(e) an effective amount up to about 25 parts by weight of an unsaturated monoglyceride of at least one straight chain fatty acid having from 8 to 22 carbon atoms and an iodine value of about 30 to 110, and
(f) 0 to 95 parts by weight water.

2. The composition according to claim 1 wherein said salt of a fatty acid ester of lactylic acid is an alkali, alkaline earth or ammonium salt.

3. The composition according to claim 1 wherein said salt of a fatty acid ester of lactylic acid is a sodium, potassium or calcium salt.

4. The composition according to claim 1 wherein said humectant is glycerine.

5. The composition according to claim 1 wherein said salt of a fatty acid ester of lactylic acid is a sodium, potassium or calcium salt and said humectant is glycerine.

6. The composition according to claim 1 in the physical form of a paste.

7. The composition according to claim 1 in the physical form of a viscous, pourable liquid.

8. A shaving cream composition comprising
(a) about 0.4 to about 1.50 parts by weight of at least one salt of a fatty acid ester of lactylic acid,
(b) about 1.40 to about 4.50 parts by weight of at least one saturated monoglyceride of a straight chain fatty acid having from 8 to 22 carbon atoms and an iodine value of 0 to about 20,
(c) about 2.0 to about 6.2 parts by weight of at least propylene glycol monoester of a saturated straight chain fatty acid having from 8 to 22 carbon atoms and an iodine value of 0 to about 20,
(d) about 2 to about 10 parts by weight of a polyhydroxylated humectant,
(e) about 1 to about 4 parts by weight of an unsaturated monoglyceride of at least one straight chain fatty acid having from 8 to 22 carbon atoms and an iodine value of about 60 to about 110, and
(f) about 70 to about 93 parts by weight water.

9. The composition according to claim 1 containing from about 30 to less than 74 parts by weight water and being in the physical form of a paste.

10. The composition according to claim 1 containing from about 74 to about 93 parts by weight water.

11. An aerosol shaving cream composition comprising, based on the total weight of (a) through (f),
(a) about 0.7 to about 1.0 parts by weight of at least one salt of a fatty acid ester of lactylic acid,
(b) about 2.25 to about 3.0 parts by weight of at least one saturated monoglyceride of a straight chain fatty acid having from 8 to 22 carbon atoms and an iodine value of 0 to about 20,
(c) about 3 to about 4 parts by weight of a propylene glycol monoester of at least one saturated straight chain fatty acid having from 8 to 22 carbon atoms and an iodine value of 0 to about 20,
(d) about 3 to about 5 parts by weight of a polyhydroxylated humectant,
(e) about 1.5 to about 2.5 parts by weight of an unsaturated monoglyceride of at least one straight chain fatty acid having from 8 to 22 carbon atoms and an iodine value of about 30 to about 110, and
(f) about 90 to about 85 parts by weight water.

12. The method of preparing a shaving cream composition comprising
(a) melt blending about 0.2 to about 20 parts by weight of a salt of a fatty acid ester of lactylic acid, about 1.2 to about 56 parts by weight saturated monoglyceride and about 0.8 to about 48 parts by weight of a saturated propylene glycol monoester, and
(b) mixing with said blend with about 1 to about 90 parts by weight of polyhydroxylated humectant, said parts by weight being based on the total composition weight.

13. The method of preparing a shaving cream composition comprising
(a) melt blending about 0.4 to about 1.50 parts by weight of a salt of a fatty acid ester of lactylic acid, about 1.40 to about 4.50 parts by weight saturated monoglyceride and about 2.0 to about 6.2 parts by weight of a saturated propylene glycol monoester,
(b) mixing with the blend formed in (a) an amount of water to form a viscous liquid composition,
(c) blending about 2-10 parts of a polyhydroxylated humectant and about 1-4 parts by weight of an unsaturated monoglyceride at a temperature of about 120°-140° F.

14. The method of preparing a shaving cream composition comprising
(a) melt blending about 0.4 to about 1.50 parts by weight of a salt of a fatty acid ester of lactylic acid, about 1.40 to about 4.50 parts by weight saturated monoglyceride and about 2.0 to about 6.2 parts by weight of a saturated propylene glycol monoester,
(b) forming solid particles of the blend formed in (a),
(c) mixing said solid particles with an amount of water to form a viscous, pourable liquid shaving cream,
(d) blending about 2-10 parts of a polyhydroxylated humectant and about 1-4 parts by weight of an unsaturated monoglyceride at a temperature of about 120°-140° F.

15. A shaving cream composition comprising
(a) about 0.2 to about 20 parts by weight of at least one salt of a fatty acid ester of lactylic acid,
(b) about 1.2 to about 56 parts by weight of at least one saturated monoglyceride of a straight chain fatty acid having from 8 to 22 carbon atoms and an iodine value of 0 to about 20,
(c) about 0.8 to about 48 parts by weight of at least one propylene glycol monoester of a saturated straight chain fatty acid having from 8 to 22 carbon atoms and an iodine value of 0 to about 20,
(d) about 1 to about 90 parts by weight of a polyhydroxylated humectant,
(e) 1 to about 25 parts by weight of an unsaturated monoglyceride of at least one straight chain fatty acid having from 8 to 22 carbon atoms and an iodine value of about 30 to about 110, and
(f) 0 to about 95 parts by weight water.

* * * * *